(12) United States Patent
Burd et al.

(10) Patent No.: US 8,343,535 B2
(45) Date of Patent: Jan. 1, 2013

(54) WOUND HEALING DRESSING AND METHODS OF MANUFACTURING THE SAME

(75) Inventors: Andrew Burd, Hong Kong (CN); Michael Wing Wai Tsang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 206 days.

(21) Appl. No.: 12/527,624

(22) PCT Filed: Feb. 25, 2008

(86) PCT No.: PCT/CN2008/000391
§ 371 (c)(1),
(2), (4) Date: Apr. 21, 2010

(87) PCT Pub. No.: WO2008/101417
PCT Pub. Date: Aug. 28, 2008

(65) Prior Publication Data
US 2010/0196448 A1    Aug. 5, 2010

Related U.S. Application Data

(60) Provisional application No. 60/891,464, filed on Feb. 23, 2007.

(51) Int. Cl.
| | |
|---|---|
| *A61K 9/70* | (2006.01) |
| *A61K 9/14* | (2006.01) |
| *A61K 33/38* | (2006.01) |
| *A61K 33/34* | (2006.01) |
| *A61K 33/32* | (2006.01) |
| *A61F 13/00* | (2006.01) |
| *A61L 15/00* | (2006.01) |
| *A01N 59/16* | (2006.01) |
| *A01N 59/20* | (2006.01) |

(52) U.S. Cl. ........ 424/443; 424/445; 424/486; 424/618; 424/630; 424/641

(58) Field of Classification Search .................. None
See application file for complete search history.

(56) References Cited

U.S. PATENT DOCUMENTS

| | | |
|---|---|---|
| 6,683,120 B2 | 1/2004 | Munro |
| 2006/0052478 A1 | 3/2006 | Madsen et al. |
| 2007/0212381 A1* | 9/2007 | DiFiore et al. ............... 424/404 |

FOREIGN PATENT DOCUMENTS

| | | |
|---|---|---|
| CN | 1202785 C | 5/2005 |
| CN | 1703434 A | 11/2005 |

OTHER PUBLICATIONS

International Search Report issued in corresponding PCT Application No. PCT/CN2008/000391, mailed Jun. 12, 2008.

* cited by examiner

*Primary Examiner* — Ernst Arnold
(74) *Attorney, Agent, or Firm* — Knobbe Martens Olson & Bear LLP

(57) ABSTRACT

Disclosed are a hydrogel dressing for covering or treating a wound and a method for preparing the same. The hydrogel dressing includes a matrix structure of a cross-linked mixture, and an elastic sheet coated with an elementary metal or ionic metal embodied in the matrix structure. The mixture comprises a hydrophilic polymer, about 0.5 to about 5 wt % of a photocatalyst agent and at least 80 wt % of water based on the total weight of the mixture.

14 Claims, No Drawings

WOUND HEALING DRESSING AND METHODS OF MANUFACTURING THE SAME

RELATED APPLICATIONS

This application is the U.S. National Phase filing under 35 U.S.C. §371 of PCT/CN2008/000391, filed Feb. 25, 2008, entitled "WOUND HEALING DRESSINGS AND METHODS OF MANUFACTURING THE SAME", which designated the United States and was published in English on Aug. 28, 2008, which claims priority under 35 U.S.C. §119(e) to United States Provisional Application No. 60/891,464, filed Feb. 23, 2007.

FIELD OF THE INVENTION

The present invention is directed to a hydrogel based dressing for covering or treating wound, such as trauma, burn, a surgical incision and a catheter insertion site.

BACKGROUND OF THE INVENTION

Wound care treatments have evolved to comprise a complex range of strategies, devices and products. These include the application of topical medicated or anti-microbial solutions, medicated and non-medicated, occlusive and non-occlusive, adherent and non-adherent dressings. In general the healing of open wounds occurs most favouably when there is absence of infection and the healing takes place in a moist environment. Healing occurs by a series and sequence of cell-cell and cell-matrix interactions and involves the formation of new tissues. The choice of a particular wound management and dressing strategy is in principle dictated by the phase of healing and factors which affect the rate of healing such as anatomical site, medical-co-morbidity, age, infection etc. At this time the most commonly used antimicrobial agent used in topical wound care is silver. The major concern with silver is that there is an almost direct correlation between antimicrobial effect and cytotoxic effect on cells involved in healing wounds.

Silver in its ionic state possesses a very broad spectrum of antimicrobial efficacy. Particularly, ionized silver has broad antibacterial, antifungal and antiviral properties which are caused by the reactivity of silver ions with a variety of functional groups. Silver ions, similar to most heavy metals in their ionized state, can complex with electron-donating functional groups containing sulfur, oxygen or nitrogen. In biological systems these electron donor groups are present as functional groups such as thiols, carboxylates, phosphates, hydroxyl, amines, imidazoles and indoles, either singly or in many varied combinations. These electron donor groups are found in great numbers in a variety of biomolecules which make up microbes. The binding of ionized silver to any of these electron donor groups causes disruption or inactivation of the biological system, resulting in the microbe's death. Depending on the source of the silver ions, studies indicate that silver ions kill the microbe either by attacking the cell wall and membrane producing blebs or by producing aggregation of nuclear material into filaments As a result, a silver or silver ion containing substance has been developed to improve conventional dressings.

A specific advantage of using a silver ion as a bacteriostatic agent is the general lack of the formation of bacterial tolerance to the compound. This is in contrast to many types of antibiotics. However a major drawback when using ionic silver for bacteriostatic purposes is the reduction of the ion to free silver which results in dark stainings. Such stainings have been reported to give potentially permanent pigmentation of the skin, which is so-called argyria.

U.S. Pat. No. 5,744,11 to Capelli discloses a "host-guest" relationship between silver ions and acyclic polyethers is accomplished through the use of excess of halide ions to keep the silver ions stable. U.S. Pat. No. 5,429,819 has disclosed a photo-stable composition comprising a complex of a silver ion and a thiosulphate salt carried on a porous particulate carrier.

The benefits of a moist healing environment have been well established but how to achieve this has been a challenge in product design. On strategy is to use occlusive dressings but another is to use a hydrating dressings. Hydrogels are of particular interest as potential hydrating dressings. They comprise a range of materials and include a permanent, three dimensional network of hydrophilic polymers; water fills the space between the polymer chains. They are available as gels, sheets and gels pre-applied to gauze. The amorphous gels are used for cavity wounds whilst sheet dressings and in pregnated gauze can be applied to surface wounds.

U.S. Pat. No. 4,871,490 discloses a sheet hydrogel dressing which is useful in keeping a wound moist but it does not have any inherent antimicrobial activity.

Thus there is to date no successful combination of a hydrogel dressing and silver ions in treating a wound. Further, there have been no reports that silver is used in a dressing in a film form.

It is known in the art $TiO_2$ in an ultra-fine powder form is a photocatalytic antimicrobial agent. However, the prior art has not taught or suggested using $TiO_2$ in a dressing as the antimicrobial agent.

The present invention is intended to provide a dressing which comprises a hydrogel base containing $TiO_2$ in combination with silver ions.

SUMMARY OF THE PRESENT INVENTION

A first aspect of the present invention is directed to a hydrogel dressing for treating a wound comprising a matrix structure of a cross-linked mixture, and an elastic sheet coated with an elementary metal or ionic metal embodied in the matrix structure. The cross-linked mixture comprises a hydrophilic polymer, about 0.5 to about 5 wt % of a photocatalyst agent and at least 80 wt % of water based on the total weight of the mixture.

A second aspect accordingly to the present invention is to provide a method of manufacturing a hydrogel dressing for treating a wound, comprising: preparing a mixture comprising at least 80 wt % of water, about 0.5 to about 5 wt % of a photocatalyst agent, and a hydrophilic polymer; providing an elastic sheet coated with an elementary metal or ionic metal; and subjecting the mixture and the elastic sheet in a mould to an ionizing radiation.

A third aspect of the present invention is directed to a method for treating a wound comprising applying the wound with a dressing described herein.

In an embodiment of the method of treating a wound, the method further comprises adding an electrical current on the hydrogel dressing of the invention.

The dressing of the invention is preferably in a non-fluid state such that it can be handled manually and conveniently, and placed on a wound easily.

DETAILED DESCRIPTION OF THE INVENTION

The term "hydrogel dressing silver sheet", "hydrogel dressing sheet", "dressing sheet" or "wound dressing" used herein refers to the dressing which is made of a gel-like substance having relatively high water content and with an elementary metal or ionic metal coated sheet prepared according to a method of the invention.

The term "a matrix structure" refers to a matrix structure formed through cross-linking a mixture mainly comprising a hydrophilic polymer which can be solidified by an ionizing radiation.

The term "treating" or "treatment" used herein means an operation carried out to a wound so as to improve the condition of the wound.

The term "wound" used herein is of the broadest meaning including but not limited to: trauma, burn, a surgical incision, a catheter insertion sit, and a medical implants site.

Also, the weight percentages (wt %), unless otherwise stated, are the wt % of ingredients based on the total weight of a mixture or composition.

A hydrogel dressing provided in the present invention is in a non-fluid state or a gel-like structure comprising a matrix structure of hydrophilic polymers and a photocatalyst agent. It cannot only be used to cover a wound to be treated, but also release an infection controlling agent to the wound and balance the moisture required by the wound. In addition, the dressing according to the invention can also absorb exudates from the wound to kill the microbes in the absorbed exudates and reduce the odor.

According to one aspect of the present invention, there provides a hydrogel dressing for treating a wound, in which a matrix structure of cross-linked polymers is formed through cross-linking a mixture comprising a polymer, at least 80 wt % of water, and 0.5 wt % to about 5 wt % of a photocatalyst agent for controlling infection of the wound.

In the hydrogel dressing an elastic sheet coated with an elementary metal or ionic metal is embodied in the matrix structure.

According to another aspect of the present invention, there provides a method of manufacturing a hydrogel dressing described herein. In an embodiment of the method according to the present invention, it comprises the steps of: (a) preparing a mixture of ingredients including at least 80 wt % of purified water, about 0.5 wt % to about 5 wt % of a photocatalyst agent for controlling infection, and a polymer; (b) immerging an elementary metal or ionic metal coated sheet in the mixture; and (c) solidifying the mixture with the metallic coated sheet immerged therein in a mould by subjecting the same to an ionizing radiation.

The photocatalyst agent used in the invention comprises titanium dioxide in an ultra-fine powder form selected from the group consisting of a hydrophilic anatase form, rutile form, anatase form, and brookite form of titanium dioxide ($TiO_2$), and titanium dioxide (B), preferably is a hydrophilic anatase form of titanium dioxide.

In embodiments of the invention, the metal element that is coated onto the elastic sheet is selected from the group consisting of a silver, zinc and copper, preferably is a silver, and more preferably is a nanoscale silver.

In the invention, the photocatalyst and the elementary metal or ionic metal provide a synergistic effect on controlling an infection of the wound, degrading organic matters and inhibiting growth of bacteria, which are double secures in inhibiting growth of microbes and yet have relatively low cytotoxic effect on wounds to be treated or the surrounding skin thereof.

It is to be noted that the above photocatalyst and the elementary metals or ionic metals used in the invention should not interfere with cross-linking of the polymers during formation of the dressing.

Experiments have shown that excessive use of the photocatalyst agent, such as $TiO_2$ would prevent the formation of the polymerized structure. Even if the matrix structure could be formed, the high content of the photocatalyst agent would damage the texture of the dressing. If the photocatalyst agent content is too low, then it would not sufficient to control infection and the wound to be treated may still be infected. Thus, the content of the photocatalyst agent as an infection control agent may often be important.

In embodiments of the invention, the dressing comprises about 0.5 wt % to about 5 wt % of $TiO_2$, and preferably comprise 0.5 wt % to 3 wt % of $TiO_2$.

In the invention, the polymers used in the mixture may be natural polymers or synthetic polymers or mixtures thereof. When the synthetic polymers are used, the content thereof in the mixture can be about 5 to 15 wt %; and when the natural polymers are used, the content thereof can be no more than 3 wt %. In a preferable embodiment, the polymer is a mixture of a synthetic polymer and a natural polymer.

The synthetic polymers that can be used in the invention are well known for one of ordinary skill in the art such as polyacrylamide polymers and polyvinyl pyrrolidone polymers. Examples of suitable polyacrylamides include but are not limited to those having an average molecule weight of about 1,000,000 Mw. Examples of suitable polyvinyl pyrrolidones include but are not limited to those have an average molecule weight of about 360,000 Mw.

The natural polymer may be selected from gelatine and agar.

Examples of suitable gelatine and agar used in the present invention include the technical grade agar.

An elastic sheet used in the invention is evident to those skilled in the art, such as polymesh sheets, polymer sheets and non-woven textile sheet (i.e. the non-woven textile used as a face mask), provided that they can be coated with the elementary metals or ionic metals used in the invention. In a preferred embodiment, a layer of silver or silver oxide will be coated by physical vapour deposition method on these substrates and provided that the target can be adhered on these substrates.

In the mixture of the invention may further include plasticizers, which are selected propylene glycol or polyhydroxy compounds having low molecular weight including glycerol, sorbitol, gluconolactone, and gluconic acid and urea.

Preferably, the cross-linked structure in the dressing comprises at least 80 wt % of water. With such a relatively high water content, the dressing according to the invention is a cushion-like and the elastic sheet increases the tensile strength of the dressing.

In the invention, the ionizing radiation may be a gamma radiation or an electron beam although any suitable radiation that could induce the cross-linking would also be appropriate. Preferably, the strength of the gamma radiation may be in the range of 25 kGy to 40 kGy. Accordingly, a hydrogel dressing or a non-fluid sheet material is obtained.

Preferably, the hydrogel dressing or the non-fluid sheet material may be a moisture balancer, an antiseptic agent or deodor agent for the wound, such as the surgical incision, the catheter insertion site, implants site, burn, or the like. Moisture release and disinfections function often necessary to wound healing.

According to another aspect of the invention, there provides a method for treating a wound comprising applying the wound with a hydrogel dressing of the invention. It can be appreciated by one skilled in the art that duration of applying and a frequency of replacement of the hydrogel dressing will depend on the site, area, depth and severity of the wound.

In an embodiment of the method of treating a wound, the method further comprises adding an electrical current on the hydro gel dressing so that an infection of microorganism such bacteria will be controlled, treated or prevented. Preferably, the electrical current is performed with a positive electrode which is placed on or incorporated in the hydrogel dressing and a negative electrode which is attached to adjacent unwounded skin. One of ordinary skill in the art will readily determine an intensity and duration of the electrical current according to the site, area, depth and severity of the wound. For example a lithium-manganese dioxide non-rechargable thin film battery has been used with a voltage range of 1.5 to 3.3 Volts with a nominal capacity of 400 mAh giving a maximum discharge of 25 mA. Such a device is supplied by Ultralife Batteries, Inc. Part#U10007. This has been used for up to one week of continuous application but changing the dressing on a daily basis. The positive electrode has been attached to the hydrogel based dressing and the negative electrode attached to skin close to the wound. The electrodes are standard Biomedical electrodes such as supplied by 3M™ UK and called Red Dot™ Adult Solid Gel electrodes.

In our study, we find the silver component enhances the current flow through the hydrogel. It is some property of the electric current which is 'enhancing' the bacterial killed in the experimental models.

EXAMPLES

The following examples are provided for purposes of illustrating the embodiments of the invention not by way of limitation to the scope of the invention. The manufacturers of raw materials utilized in the examples can be obtained from DuPont, BASF, Clariant, Oxoid, and Sigma Chemical.

Example 1

A mixture solution was prepared by mixing the following ingredients together.

| Ingredients | Contents (parts by weight) |
|---|---|
| Anatase form of TiO2 | 1 |
| Poly vinyl-pyrolidone | 10.5 |
| Polyethylene glycol | 2.5 |
| Agar | 1.5 |
| Purified water | 84.5 |
| Total | 100 |

A piece of a nanoscale silver ion (silver oxide) coated polymesh is also provided in this Example.

The above ingredients were mixed together in a cleanroom environment and a mixture in the form of a solution was produced. The mixture solution was then poured into a Petri dish of suitable size such that the mixture solution formed a liquid layer with a thickness of about 2 mm. Then, one piece of nanoscale silver ion coated polymesh was placed on top of the liquid layer and the solution was further poured into the mould until full thickness thereof. The Petri dish was then tightly covered with a polyethylene film heat-sealing around the edges thereof. The Petri dish together with the solution therein was exposed to a gamma radiation of 25 kGy. The solution then became solidified forming a non-fluid sheet after the crosslinking of polyvinyl pyrolidine and agar and the silver coated polymesh incorporated inside the hydrogel sheet dressing.

Example 2

A mixture solution was prepared by mixing the following ingredients together.

| Ingredients | Contents (parts by weight) |
|---|---|
| Anatase form of TiO$_2$ | 3 |
| Poly vinyl-pyrolidone | 6 |
| Polyethylene glycol | 1.5 |
| Agar | 2 |
| Purified water | 88 |
| Total | 100 |

A piece of nanoscale silver coated polymesh which can be obtained from Maxford Medical and/or Smith & Nephew, is also needed in this Example.

Similar to Example 1, the above ingredients were mixed together in a clean environment and the mixture solution was formed. The mixture solution was then processed following the same steps as in Example 1, except a gamma radiation with a strength of 35 kGy was applied.

A dressing formed from the above method exhibited properties similar to the dressing obtained from Example 1.

Examples 3 and 4

The above two examples were repeated but during the radiation step, the solution was exposed to an electron beam instead of gamma radiation. The resultant dressings were also found to possess similar characteristics and effectiveness.

It is understood that anatase form of titanium dioxide was used as an agent which oxidizes and degrades organic matters inhibiting bacteria growth and reducing the odor. Polyvinyl-pyrolidone is a synthetic polymer which is cross-linkable to form a cross-linked matrix structure. Polyethylene glycol was used as a plasticizing agent enhancing the physical properties of the dressing. Agar is a natural polymer and is also cross-linkable to form a gel-like substance. When the solution as in the example was exposed to the radiation, the solution became solidified and a sheet-like dressing was formed.

A dressing made by the above method is sterile, elastic, disinfecting and deodorant. Due to the disinfecting nature of the dressing, no additional disinfectant was applied to the wound. Due to the cross-linked matrix structure of the dressing, it was able to absorb exudates from wound treated therewith and minimized the change of dressings. Due to the relatively high water content and elastic nature of the dressing, it was gentle to the wound and kept the moist environment of the wound. Due to the presence of the infection-controlling agent, infection of the wound became very unlikely. It is also to be noted that unlike conventional dressings which become no longer sterile once they are exposed to the surroundings, a hydrogel dressing made in accordance with the present invention remained sterile even after it was exposed to the surroundings. Due to the presence of photocatalyst, the organic matters causing odor from wound was degraded and eliminated. Due to the nanoscale silver coated polymesh, electric current was conducted to practice electrotherapy of wound healing. The sheet structure of the dressing conformed to the wound very well and provided a barrier to bacteria from the surroundings. The dressing with these characteristics together is desirable for enhanced wound healing.

All of above patents, patent application publications and non-patent publications referred to the specification are incorporated herein by reference, in their entireties.

For the foregoing it will be appreciated that, although the specific embodiments of the invention have been described for purposes of illustration, various varieties and modifications can be made without deviating from the spirit and the scope of the invention as defined by the appended claims.

The invention claimed is:

1. A hydrogel dressing for treating a wound comprising:
    a matrix structure of a cross-linked mixture, and
    an elastic sheet coated with an elementary metal or ionic metal embodied in the matrix structure,
    wherein the mixture comprises a hydrophilic polymer which is a combination of a synthetic polymer and a natural polymer, wherein the synthetic polymer comprises polyacrylamide or polyvinylpyrrolidone or a combination thereof, and the natural polymer comprises gelatine or agar or a combination thereof and the dressing comprises about 5 wt % to about 15 wt % of the synthetic polymer, and no more than 3 wt % of the natural polymer, about 0.5 to about 5 wt % of a photocatalyst agent and at least 80 wt % of water based on the total weight of the mixture.

2. The dressing of claim 1, wherein the photocatalyst agent comprises an ultra-fine titanium dioxide selected from the group consisting of a rutile form, an anatase form, a brookite form, titanium dioxide (B) and a combination thereof.

3. The dressing of claim 1 further comprising a plasticizing agent selected from the group consisting of polyethylene glycol and polypropylene glycol.

4. The dressing of claim 1, wherein the metal is selected from the group consisting of a silver, zinc, and a copper.

5. The dressing of claim 4, wherein the silver is in a nanocrystalline form.

6. A method of manufacture of a dressing for treating a wound, comprising:
    (a) preparing a mixture comprising at least 80 wt % of water, 0.5 to 5 wt % of a photocatalyst agent, and a hydrophilic polymer which is a combination of a synthetic polymer and a natural polymer; wherein the synthetic polymer comprises polyacrylamide or polyvinylpyrrolidone or a combination thereof, and the natural polymer comprises gelatine or agar or a combination thereof and the dressing comprises about 5 wt % to about 15 wt % of the synthetic polymer, and no more than 3 wt % of the natural polymer,
    (b) providing an elastic sheet coated with an elementary metal or ionic metal; and
    (c) subjecting the mixture and the elastic sheet in a mould to an ionizing radiation.

7. A method of treating a wound in a subject comprising applying a hydrogel dressing to the wound, wherein said hydrogel dressing comprises:
    a matrix structure of a cross-linked mixture; and
    an elastic sheet coated with an elementary metal or ionic metal embodied in the matrix structure,
    wherein said mixture comprises a hydrophilic polymer which is a combination of a synthetic polymer and a natural polymer, wherein the synthetic polymer comprises polyacrylamide or polyvinylpyrrolidone or a combination thereof, and the natural polymer comprises gelatine or agar or a combination thereof and the dressing comprises about 5 wt % to about 15 wt % of the synthetic polymer, and no more than 3 wt % of the natural polymer, about 0.5 to about 5 wt % of a photocatalyst agent and at least 80 wt % of water based on the total weight of the mixture.

8. The method of claim 7, further comprising applying an electrical current to the dressing.

9. The method of claim 8, wherein the electrical current is applied with a positive electrode which is placed on or incorporated in the dressing, and a negative electrode which is attached to skin close to the wound.

10. The method of claim 7, wherein the photocatalyst agent comprises an ultra-fine titanium dioxide selected from the group consisting of a rutile form, an anatase form, a brookite form, titanium dioxide (B) and a combination thereof.

11. The method of claim 7, further comprising a plasticizing agent selected from the group consisting of polyethylene glycol and polypropylene glycol.

12. The method claim 7, wherein the metal is selected from the group consisting of silver, zinc, copper and a combination thereof.

13. The method of claim 12, wherein the silver is in a nanoscale.

14. The method of claim 13, wherein the elastic sheet is a nanoscale silver coated polymesh, a non-woven textile or a polymer film.

* * * * *